(12) United States Patent
Cheng et al.

(10) Patent No.: US 7,001,421 B2
(45) Date of Patent: Feb. 21, 2006

(54) STENT WITH PHENOXY PRIMER COATING

(75) Inventors: Peiwen Cheng, Santa Rosa, CA (US); Rangarajan Sundar, Santa Rosa, CA (US); Kaushik A. Patel, Windsor, CA (US); Kishore Udipi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 213 days.

(21) Appl. No.: 10/376,860

(22) Filed: Feb. 28, 2003

(65) Prior Publication Data

US 2004/0172120 A1    Sep. 2, 2004

(51) Int. Cl.
*A61F 2/06* (2006.01)
(52) U.S. Cl. ............... 623/1.11; 623/1.15; 623/1.42
(58) Field of Classification Search ........... 623/1.12, 623/1.15, 1.11, 1.42
See application file for complete search history.

(56) References Cited

U.S. PATENT DOCUMENTS

| | | | |
|---|---|---|---|
| 4,739,762 A * | 4/1988 | Palmaz | ............ 623/1.11 |
| 5,464,650 A | 11/1995 | Berg et al. | |
| 5,624,411 A | 4/1997 | Tuch | |
| 5,679,400 A | 10/1997 | Tuch | |
| 5,776,184 A | 7/1998 | Tuch | |
| 5,779,729 A | 7/1998 | Severini | |
| 5,824,048 A | 10/1998 | Tuch | |
| 5,837,008 A | 11/1998 | Berg et al. | |
| 5,873,904 A * | 2/1999 | Ragheb et al. | ............ 623/1.13 |
| 6,013,855 A * | 1/2000 | McPherson et al. | ...... 623/23.76 |
| 6,099,563 A | 8/2000 | Zhong | ............ 623/1.46 |
| 6,214,901 B1 | 4/2001 | Chudzik et al. | |
| 6,231,600 B1 | 5/2001 | Zhong | |
| 6,251,136 B1 | 6/2001 | Guruwaiya et al. | |
| 6,344,035 B1 | 2/2002 | Chudzik et al. | |
| 6,383,215 B1 | 5/2002 | Sass | |
| 6,455,035 B1 | 9/2002 | Suri et al. | |
| 6,663,662 B1 * | 12/2003 | Pacetti et al. | ............ 623/1.13 |
| 2001/0014717 A1 | 8/2001 | Hossainy | ............ 525/60 |

* cited by examiner

*Primary Examiner*—Corrine McDermott
*Assistant Examiner*—Thomas J. Sweet

(57) ABSTRACT

The present invention provides a system for treating a vascular condition, which includes a catheter; a stent coupled to the catheter, the stent including a stent framework; a phenoxy primer coating operably disposed on the stent framework; and a drug-polymer coating disposed on the phenoxy primer coating. The present invention also provides a drug-coated stent and a method of manufacturing a drug-coated stent.

24 Claims, 4 Drawing Sheets

STENT WITH PHENOXY PRIMER COATING

FIELD OF THE INVENTION

This invention relates generally to biomedical stents. More specifically, the invention relates to a primer for a stent that may be subsequently coated with a drug polymer.

BACKGROUND OF THE INVENTION

Endovascular stents are coated frequently with a drug polymer that contains one or more therapeutic compounds within a polymeric matrix to improve the efficacy of the stents. These compounds are eluted from the stent coating to the tissue bed surrounding the implanted stent. The effectiveness of these drugs is generally improved because localized levels of medication may be higher and potentially more successful than orally or intravenously delivered drugs, which are distributed throughout the body rather than concentrated at the location of most need. Drugs released from tailored stent coatings may have controlled, timed-release qualities, eluting their bioactive agents over hours, weeks or even months. A common solvent or a pair of solvents may be used to dissolve drugs and polymers, including copolymers, terpolymers or polymer blends. Then the drug-polymer solution is sprayed or dipped on the stent. Upon drying, the drug-polymer coating is formed on the stent surface.

Polymer matrices containing the compounds must be reliably attached to the stent to control delivery of the pharmaceutical compounds, to maintain high quality during manufacturing of such a stent, and to prevent cracking or flaking of the drug-polymer coating when the stent is deployed. Problems may arise in getting coatings to adhere to stents, particularly stents made of stainless steel. Most coronary stents are made of stainless steel or tantalum and are finished by electrochemical polishing for surface smoothness. A smooth surface is desirable because early research has shown that a stent with a rough surface results in more platelet cell adhesion, thrombus, inflammation, and restenosis than a smoothly polished stent. The smooth surface may pose a challenge to the coating, however. Due to the very different nature of the polymer and the metallic substrate, polymers do not easily adhere to the metallic substrate. If the coating does not adhere well to the metal surface, it may cause problems such as coating delamination, irregular drug release profiles, or embolism caused by broken and detached debris from the coating.

The coating may crack or fall off during assembly, packaging, storage, shipping, preparation and sterilization prior to deployment unless effectively adhered to the stent framework. Degradation of the polymer coating may occur with prolonged exposure to light and air, as the constituents of the drug polymer may oxidize or the molecular chains may scission. Although degradation of the polymer coating is of major concern, it is imperative that the adhesion strength of the coating be greater than the cohesive strength of the polymeric matrix to avoid any loss of the coating.

Polymeric coatings have a tendency to peel or separate from an underlying metallic stent because of low adhesion strength typically found between polymers and metals. Many polymers are non-polar or have limited polarization, reducing their ability to stick to the metal stent framework. Temperature excursions of the coated stent and the difference in thermal expansion coefficients between the metal and the coating may contribute to the fatigue and failure of the bond. Materials that are optimal for drug compatibility and elution may not, in and of themselves, provide sufficient adhesion to a metal substrate. A method to improve the adhesion between a drug-polymer coating and a metallic stent, while retaining the therapeutic characteristics of the drug-polymer stent, would be beneficial. Conventional polymers could be incorporated into the drug-polymer coating. If the adhesive strength of the polymeric coating were improved, a more robust stenting device could be made. The coating profiles may be lower and the stent struts could touch. It is desired to have an adhesion layer or primer that is biocompatible, promotes good adhesion between metals and polymers, is easy to process, and is reliable.

It is an object of this invention, therefore, to provide a drug-coated stent with an effective adhesion layer between the drug polymer and the underlying stent framework, to provide a method for manufacturing a drug-polymer coating on a metallic stent, to provide a system for treating heart disease and other vascular conditions using drug-eluting stents with improved adhesion between the drug polymer and the stent, and to overcome the deficiencies and limitations described above.

SUMMARY OF THE INVENTION

One aspect of the invention provides a system for treating a vascular condition, which includes a catheter; a stent coupled to the catheter, the stent including a stent framework; a phenoxy primer coating operably disposed on the stent framework; and a drug-polymer coating disposed on the phenoxy primer coating. The catheter may include a balloon used to expand the stent and a sheath that retracts to allow expansion of the stent.

Another aspect of the present invention provides a drug-coated stent including a stent framework, a phenoxy primer coating disposed on the stent framework, and a drug-polymer coating disposed on the phenoxy primer coating. The stent framework may have a metallic or polymeric base.

Another aspect of the present invention provides a method of manufacturing a drug-coated stent. A phenoxy resin is mixed with a solvent to form a phenoxy resin solution, the phenoxy resin solution is applied onto a stent framework, and the phenoxy resin solution is dried. A drug-polymer coating may be applied to the dried phenoxy resin solution disposed on the stent framework.

BRIEF DESCRIPTION OF THE DRAWINGS

The present invention is illustrated by the accompanying drawings of various embodiments and the detailed description given below. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings, wherein:

DETAILED DESCRIPTION OF THE PRESENTLY PREFERRED EMBODIMENTS

A phenoxy resin may be used as an effective primer coating to promote adhesion between a metal stent surface and a subsequent polymer coating. The phenoxy may be applied to the stent and dried, followed by the drug polymer being applied. The subsequent polymer coating may contain one or more therapeutic compounds to provide pharmaceutical properties to the drug-coated stent. The primer coating acts as a bridge between substrates and organic polymer coatings, with good adhesion properties to the metal and to the drug polymer.

The phenoxy resin is a high molecular weight, linear polymer derived from a parent epoxy polymer. Phenoxy resins have hydroxyl groups as opposed to the highly reactive oxirane groups of epoxy resins. The phenoxy resins are very stable thermoplastic materials and can be processed like other plastics.

Phenoxy resins are typically amorphous, and tend to not crystallize or build up stress concentrations. They may contain few or no additives, and have a low order of residual solvents, monomers, and low molecular weight extracts that might otherwise contaminate interfaces. The phenoxy primer combines beneficial characteristics of toughness and flexibility. The phenoxy primer may be cross-linked with the inclusion of a material such as isocyanate to control the hardness. The phenoxy primer coating may include a cross-linking agent such as isocyanate.

One aspect of the present invention is a system for treating coronary heart disease and other vascular conditions, using catheter-deployed endovascular stents with polymeric coatings that include one or more drugs with desired timed-release properties and a phenoxy primer coating that serves as an adhesion promoter or an adhesion layer between the stent and the drug polymer. Treatment of vascular conditions may include the prevention or correction of various ailments and deficiencies associated with the cardiovascular system, urinogenital systems, biliary conduits, abdominal passageways and other biological vessels within the body.

Figure 1:
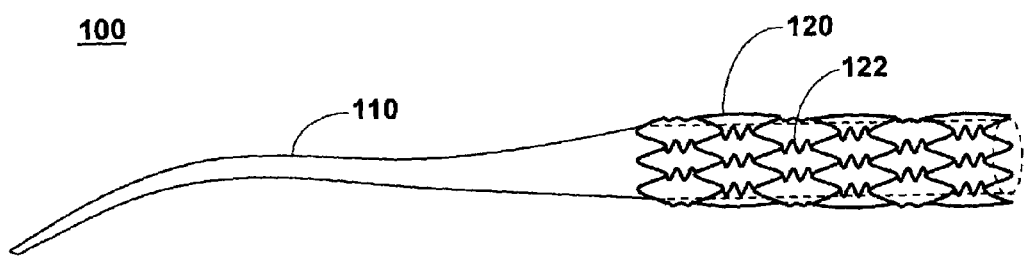
FIG. 1 is an illustration of one embodiment of a system for treating a vascular condition including a catheter, a stent, a phenoxy primer coating, and a drug-polymer coating, in accordance with the current invention.

One embodiment of a system for treating a vascular condition, in accordance with the present invention, is illustrated in FIG. 1 at 100. Vascular condition treatment system 100 may include a catheter 110, a stent 120 coupled to catheter 110, and a drug-polymer coating 122 with an underlying phenoxy primer coating on the stent or stent framework.

Stent 120 is coupled to catheter 110, and may be deployed, for example, by pressurizing a balloon coupled to the stent or by retracting a sheath that allows the stent to expand to a prescribed diameter. Stent 120 includes a stent framework. The stent framework may be formed from a metallic base such as stainless steel, nitinol, tantalum, MP35N alloy, platinum, titanium, a suitable biocompatible alloy, or other suitable metal alloy. The stent framework may be formed from a polymeric base.

The phenoxy primer coating may be disposed on the stent framework. The phenoxy primer coating may comprise, for example, a phenoxy resin or a phenoxy polymer. The phenoxy resin has hydroxyl and ether groups that link to the underlying stent material to improve the adhesion between the phenoxy primer coating and the stent framework. The ether linkages and pendant hydroxyl groups improve wettability and bonding to the stent material and to additional polymeric coatings.

A drug polymer may be disposed on the stent framework. The drug polymer may be applied to the stent after the phenoxy primer coating is disposed on the stent framework. The adhesion of the drug polymer to a stent coated with a polymeric primer layer or coating would be enhanced because the drug polymer would essentially be coating over similar material.

Drug-polymer coating 122 may include one or more drugs. Each drug may include a bioactive agent. The bioactive agent may be a pharmacologically active drug or bioactive compound. The bioactive agent may be eluted from the drug-polymer coating when the stent has been deployed in the body. Elution refers to the transfer of the bioactive agent out from drug-polymer coating 122. The elution rate is determined by the rate at which the bioactive agent is excreted from drug-polymer coating 122 into the body. The composition of the drug-polymer coating and the interdispersed drugs may control the elution rate of the bioactive agent. The phenoxy primer coating underlying drug-polymer coating 122 would tend not to be eluted, metabolized, or discarded by the body.

The drug-polymer coating may be subject to degradation during processing, packaging, sterilization, or storage of a drug-polymer coated stent. During sterilization, for example, oxidation of the drug or polymer may occur, resulting in hydrolytic damage, cleavage of the polymeric bonds, breakdown of the polymer and/or drug, or actual cracking or peeling of the drug-polymer coating. Temperature excursions of the in-process or processed stent may incite delamination of all or a portion of the drug-polymer coating. The present invention solves this problem through the use of a phenoxy primer coating between the polymer-drug coating and the metallic stent, so as to reduce or prevent drug-polymer delamination.

Upon insertion of catheter 110 and stent 120 with drug-polymer coating 122 into a directed vascular region of a human body, stent 120 may be expanded by applying pressure to a suitable balloon inside the stent, or by retracting a sheath to allow expansion of a self-expanding stent. Balloon deployment of stents and self-expanding stents are well known in the art. Catheter 110 may include a balloon used to expand stent 120. Alternatively, catheter 110 may include a sheath that retracts to allow expansion of the stent.

Figure 2:
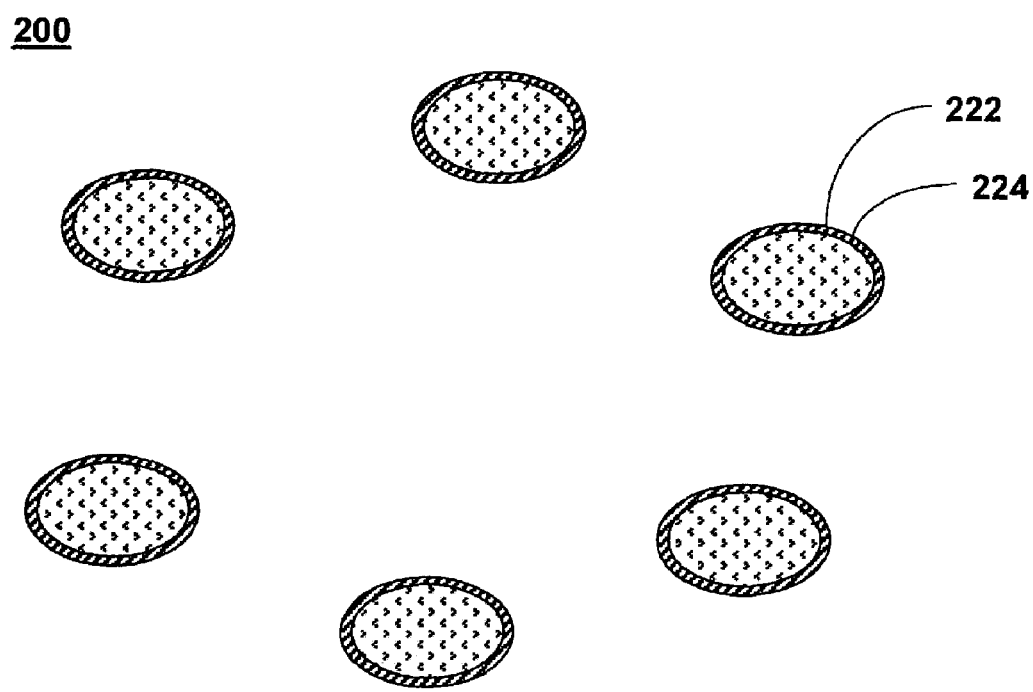
FIG. 2 is an illustration of a stent cross-section with a phenoxy primer coating on the stent surface, in accordance with the current invention.

FIG. 2 shows an illustration of a stent cross-section including a phenoxy primer coating on the stent surface, in accordance with the present invention at 200. Phenoxy coated stent 200 with may include a phenoxy primer coating 222 on a stent framework 224. Phenoxy primer coating 222 may contain phenoxy resin or any suitable form of phenoxy polymer. Phenoxy primer coating 222 may contain a polymeric matrix with an interdispersed phenoxy resin. A drug-polymer coating may be disposed on top of phenoxy primer coating 222.

Stent framework 224 may include a metallic or polymeric base. Stent framework 224 may include a base material of stainless steel, nitinol, tantalum, an MP35N alloy, platinum, or titanium. The stent or stent framework may include a base material of a suitable biocompatible alloy, a suitable biocompatible material including a biodegradable polymeric material, or a combination thereof.

Figure 3:
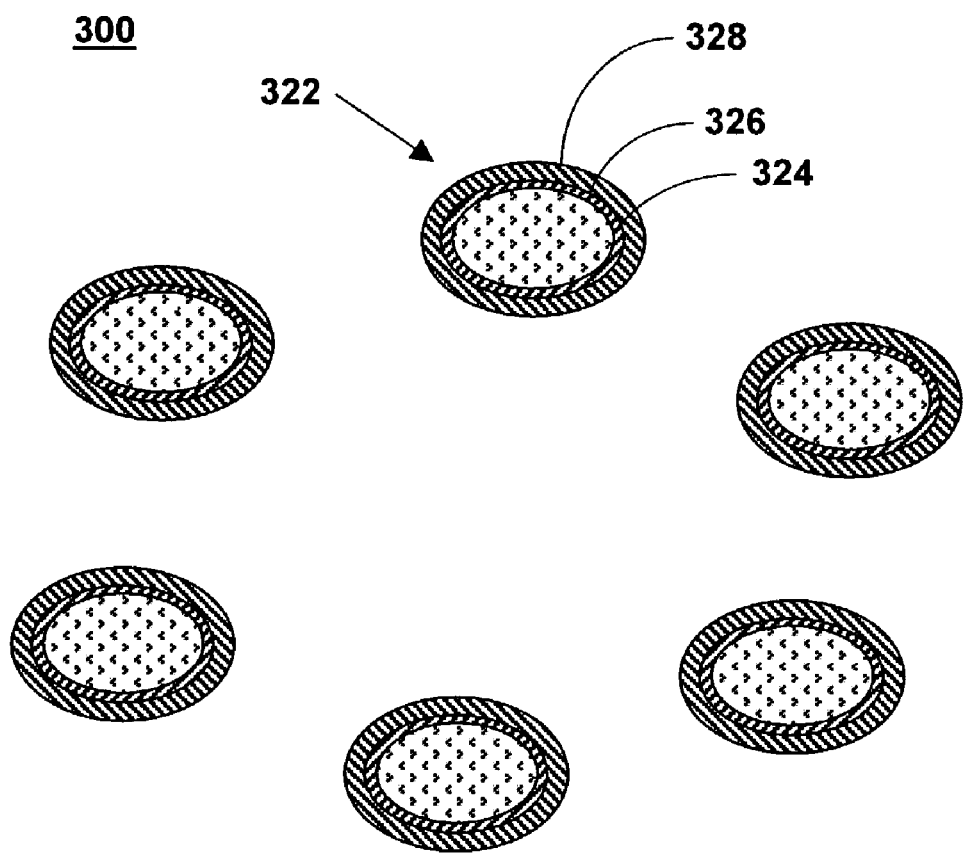
FIG. 3 is an illustration a cross section of a drug-coated stent with a phenoxy primer coating between a drug-polymer coating and the stent framework, in accordance with the current invention.

FIG. 3 shows an illustration of a stent cross-section comprised of a polymeric coating containing a drug-polymer coating disposed on a phenoxy primer coating between the drug-polymer coating, and the stent framework, in accordance with another embodiment of the present invention at 300. Drug-coated stent 300 with polymeric coating 322 includes phenoxy primer coating 326 on a stent framework 324 and a drug-polymer coating 328 on phenoxy primer coating 326. Phenoxy primer coating 326 may be referred to herein as an adhesive coating. Drug-polymer coating 328 includes at least one interdispersed bioactive agent. Phenoxy primer coating 326 may be void or nearly void of pharmaceutical drugs.

Phenoxy primer coating 326 may be selected to improve the adhesion and minimizing the likelihood of delamination of the polymeric coating from stent framework 324. Metal-adhering attributes of the primer layer aid in the cohesiveness of the polymeric coating to metallic stents. Stent framework 324 may comprise a metallic or a polymeric base.

Phenoxy primer coating 326 may be comprised of a phenoxy resin or phenoxy material that enhances adhesion between drug-polymer coating 328 and stent framework 324. Phenoxy primer coating 326 may comprise a long-chain polymer with predominantly phenoxyl groups along the backbone.

The drugs may be encapsulated in drug-polymer coating 328 using a microbead, microparticle or nanoencapsulation technology with albumin, liposome, ferritin or other biodegradable proteins and phospholipids, prior to application on the primer-coated stent.

The bioactive agent may include an antineoplastic agent such as triethylene thiophosphoramide, an antiproliferative agent, an antisense agent, an antiplatelet agent, an anti-thrombogenic agent, an anticoagulant, an antibiotic, an anti-inflammatory agent, a gene therapy agent, an organic drug, a pharmaceutical compound, a recombinant DNA product, a recombinant RNA product, a collagen, a collagenic derivative, a protein, a protein analog, a saccharide, a saccharide derivative, or combinations thereof.

The bioactive agent may be any therapeutic substance that provides a therapeutic characteristic for the prevention and treatment of disease or disorders. An antineoplastic agent may prevent, kill, or block the growth and spread of cancer cells in the vicinity of the stent. An antiproliferative agent may prevent or stop cells from growing. An antisense agent may work at the genetic level to interrupt the process by which disease-causing proteins are produced. An antiplatelet agent may act on blood platelets, inhibiting their function in blood coagulation. An antithrombogenic agent may actively retard blood clot formation. An anticoagulant may delay or prevent blood coagulation with anticoagulant therapy, using compounds such as heparin and coumarins. An antibiotic may kill or inhibit the growth of microorganisms and may be used to combat disease and infection. An anti-inflammatory agent may be used to counteract or reduce inflammation in the vicinity of the stent. A gene therapy agent may be capable of changing the expression of a person's genes to treat, cure or ultimately prevent disease. An organic drug may be any small-molecule therapeutic material. A pharmaceutical compound may be any compound that provides a therapeutic effect. A recombinant DNA product or a recombinant RNA product may include altered DNA or RNA genetic material. Bioactive agents of pharmaceutical value may also include collagen and other proteins, saccharides, and their derivatives.

For example, the bioactive agent may be selected to inhibit vascular restenosis, a condition corresponding to a narrowing or constriction of the diameter of the bodily lumen where the stent is placed. The bioactive agent may generally control cellular proliferation. The control of cell proliferation may include enhancing or inhibiting the growth of targeted cells or cell types.

The bioactive agent may be an agent against one or more conditions including coronary restenosis, cardiovascular restenosis, angiographic restenosis, arteriosclerosis, hyperplasia, and other diseases and conditions. For example, the bioactive agent may be selected to inhibit or prevent vascular restenosis, a condition corresponding to a narrowing or constriction of the diameter of the bodily lumen where the stent is placed. The bioactive agent may generally control cellular proliferation. The control of cell proliferation may include enhancing or inhibiting the growth of targeted cells or cell types.

The bioactive agent may include podophyllotoxin, etoposide, camptothecin, a camptothecin analog, mitoxantrone, rapamycin, and their derivatives or analogs. Podophyllotoxin is an organic, highly toxic drug that has antitumor properties and may inhibit DNA synthesis. Etoposide is an antineoplastic that may be derived from a semi-synthetic form of podophyllotoxin to treat monocystic leukemia, lymphoma, small-cell lung cancer, and testicular cancer. Camptothecin is an anticancer drug that may function as a topoisomerase inhibitor. Related in structure to camptothecin, a camptothecin analog such as aminocamptothecin may be used as an anticancer drug. Mitoxantrone is also an important anticancer drug, used to treat leukemia, lymphoma, and breast cancer. Rapamycin or sirolimus is a medication that may interfere with the normal cell growth cycle and may be used to reduce restenosis. The bioactive agent may also include analogs and derivatives of these agents. Antioxidants may be beneficial on their own rights for their antirestonetic properties and therapeutic effects.

Drug-polymer coating 328 may soften, dissolve or erode from the stent to elute at least one bioactive agent. This elution mechanism may be referred to as surface erosion where the outside surface of the drug-polymer coating dissolves, degrades, or is absorbed by the body; or bulk erosion where the bulk of the drug-polymer coating biodegrades to release the bioactive agent. Eroded portions of the drug-polymer coating may be absorbed by the body, metabolized, or otherwise expelled.

The pharmaceutical drug may separate within drug-polymer coating 328 and elute the bioactive agent. Alternatively, the pharmaceutical drug may erode from drug-coated stent 300 and then separate into the bioactive agent. Drug-polymer coating 328 may include multiple pharmaceutical drugs, and more than one adhesion promoter. Drug-polymer coating 328 may include a single bioactive agent with various adhesion promoters to secure the bioactive agent to phenoxy primer coating 326 and stent framework 324. Drug-polymer coating 328 may comprise one or more adhesion promoters.

Drug-polymer coating 328 may also include a polymeric matrix. For example, the polymeric matrix may include a caprolactone-based polymer or copolymer, or various cyclic polymers. The polymeric matrix may include various synthetic and non-synthetic or naturally occurring macromolecules and their derivatives. The polymeric matrix may include biodegradable polymers such as polylactide (PLA), polyglycolic acd (PGA) polymer, poly (e-caprolactone) (PCL), polyacrylates, polymethacryates, or other copolymers. The pharmaceutical drug may be dispersed throughout the polymeric matrix. The pharmaceutical drug or the bioactive agent may diffuse out from the polymeric matrix to elute the bioactive agent. The pharmaceutical drug may diffuse out from the polymeric matrix and into the biomaterial surrounding the stent. The bioactive agent may separate from within drug-polymer coating 328 and diffuse out from the polymeric matrix into the surrounding biomaterial. In a further embodiment the drug coating composition may be fashioned using the drug 42-Epi-(tetrazolyl)-rapamycin, set forth in U.S. Pat. No. 6,329,386 assigned to Abbott Laboratories, Abbott Park, Ill. and dispersed within a coating fashioned from phosphorylcholine coating of Biocompatibles International P.L.C. set forth in U.S. Pat. No. 5,648,442.

The polymeric matrix may be selected to provide a desired elution rate of the bioactive agent. The pharmaceutical drugs may be synthesized such that a particular bioactive agent may have two different elution rates. A bioactive agent with two different elution rates, for example, would allow rapid delivery of the pharmacologically active drug within twenty-four hours of surgery, with a slower, steady delivery of the drug, for example, over the next two to six months. The phenoxy primer coating may be selected to firmly secure the polymeric matrix to the stent framework, the polymeric matrix containing the rapidly deployed bioactive agents and the slowly eluting pharmaceutical drugs.

Figure 4:
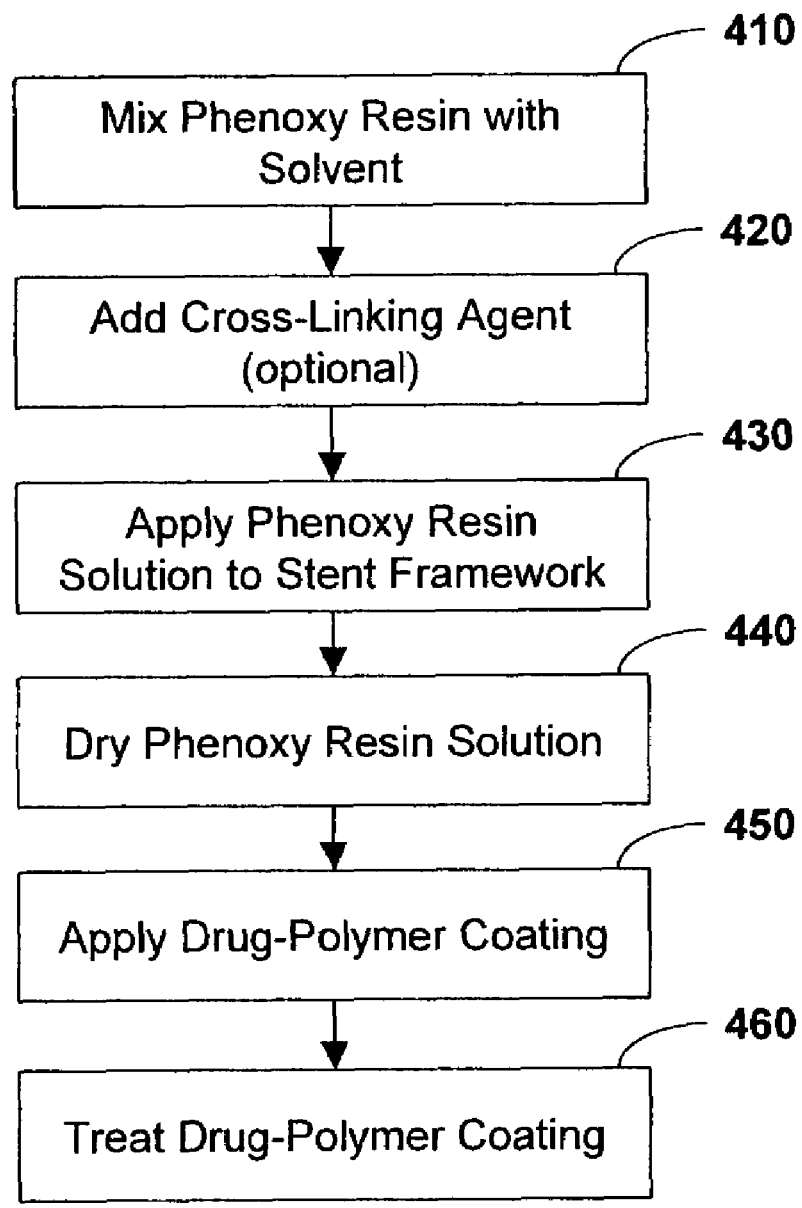
FIG. 4 is a flow diagram of one embodiment of a method for manufacturing a drug-coated stent, in accordance with the current invention.

Another aspect of the current invention is a method of manufacturing, a drug-coated stent with a phenoxy primer coating. FIG. 4 shows a flow diagram of one embodiment of a method for manufacturing a drug-coated stent that includes a phenoxy primer coating, in accordance with the present invention at 400.

The drug-coated stent with phenoxy primer coating is manufactured by mixing a phenoxy resin with a solvent to form a phenoxy resin solution, as seen at block 410. Choloroform may be used as the solvent. An alcohol such as methanol or ethanol, acetone, or other suitable solvent may be used to form the solution. The phenoxy resin solution may contain, for example, 1–2% phenoxy in a chloroform solvent.

A cross-linking agent may be added to the phenoxy resin solution, as seen at block 420. Isocyanate or any other suitable agent for cross-linking the phenoxy polymer may be used as the cross-linking agent. The cross-linking agent may be used to provide additional hardness to the phenoxy coating, when additional hardness is desired.

The phenoxy resin solution is applied to a metallic or polymeric stent framework, as seen at block 430. The phenoxy resin solution may be applied to the stent framework by dipping, spraying, painting, brushing, or by other suitable methods. Prior to primer application, the stent may be cleaned using, for example, various degreasers, solvents, surfactants and de-ionized water as is known in the art.

The phenoxy resin solution disposed on the stent framework is dried, as seen at block 440. Excess liquid may be blown off prior to drying the film. Drying of the polymeric solution to eliminate or remove any volatile components may be done at room temperature or elevated temperatures under a dry nitrogen or other suitable environment including a vacuum environment. The coated stent may be baked at moderately elevated temperatures on the order of 100 degrees centigrade to drive off any solvent trapped inside the primer coating, and to provide thermal energy for cross linking the phenoxy polymer with the optional cross-linking agent. A second dipping and drying step may be used to thicken the coating if needed. The thickness of the phenoxy primer coating may range between 0.2 microns and 0.6 microns or greater in order to adequately coat the stent framework and to provide a satisfactory underlayer for subsequent drug-polymer application. The weight of the phenoxy primer coating depends on the diameter and length of the stent, though a typical weight of the phenoxy primer coating is between 20 micrograms and 70 micrograms. Additional application and drying steps may be included to reach the desired thickness of the primer coating.

A drug-polymer coating may be applied to the phenoxy primer coating, as seen at block 450. The drug polymer may be mixed in a suitable solvent, and applied over the primer using an application technique such as dipping, spraying, painting or brushing. During the coating operation, the drug-polymer adheres well to the phenoxy primer coating.

The drug-polymer coating may be applied immediately after the phenoxy primer coating is applied. Alternatively, drug-polymer coatings may be applied to a stent with the phenoxy primer coating at a later time.

A drug polymer may be mixed with a suitable solvent to form a polymeric solution. The drug polymer may include a polymeric matrix and one or more therapeutic compounds.

To form a drug-polymer coating, a monomer such as a vinyl acetate derivative may be mixed with other monomers in a solvent such as isopropyl alcohol to form a polymeric solution. The mixture may be reacted to form a polymer, and one or more bioactive agents may be mixed with the polymerized mixture to form a drug polymer with a predefined elution rate. A suitable bioactive agent or a solution containing the bioactive agent may be mixed in with the polymeric solution. Alternatively, a polymer such as a copolyester or block copolymer may be dissolved in a suitable solvent, and one or more bioactive agents may be added to the mixture. The mixture may be combined with an adhesion promoter in the polymeric solution. One or more adhesion promoters may be selected and added to the mixture.

The polymeric solution may be applied to the stent framework with the phenoxy primer coating. The polymeric solution may be applied to the stent using any suitable method for applying the polymer solution.

Excess liquid may be blown off and the polymeric solution dried. Drying of the polymeric solution to eliminate or remove any volatile components may be done at room temperature or elevated temperatures under a dry nitrogen or other suitable environment. A second dipping and drying step may be used to thicken the coating. The thickness of the drug-polymer coating may range between 1.0 microns and 200 microns or greater in order to provide sufficient and satisfactory pharmacological benefit with the bioactive agent.

The drug-polymer coating may be treated, as seen at block 460. Treatment of the drug-polymer coating may include air drying or low-temperature heating in air, nitrogen, or other controlled environment. The drug-polymer coating may be treated by heating the drug-polymer coating to a predetermined temperature.

The coated stent with the drug-polymer coating disposed on the phenoxy primer coating may be coupled to a catheter. The coated stent may be integrated into a system for treating vascular conditions such as heart disease, by assembling the coated stent onto the catheter. Finished coated stents may be reduced in diameter and placed into the distal end of the catheter, formed, for example, with an interference fit that secures the stent onto the catheter. The catheter along with the drug-coated stent may be sterilized and placed in a catheter package prior to shipping and storing. Additional sterilization using conventional medical means occurs before clinical use.

More specifically, illustrative examples of the present invention are provided herein.

EXAMPLE 1

Phenoxy Resin Solution Formulation

One embodiment of the present invention is exhibited by the formulation of a phenoxy resin solution based on a phenoxy resin mixed in a chloroform solvent.

An amount of phenoxy resin weighing 2.236 g is placed in a glass bottle. The phenoxy, referred to as phenoxy PKHC and identified as phenol, 4,4'-(1-methylethylidene)bispolymer with (chloromethyl) oxirane, may be obtained from Phenoxy Specialties, 800 Cel-River Road, Rock Hill, S.C. 29730. Chloroform in the amount of 148.4 milliliters is added. The contents are shaken until all the polymers are dissolved. The solution may be split, some of which may be used for coating stents, the remaining of which may be used for coating metallic coupons.

EXAMPLE 2

Dip Coating Process

A coating process for disposing a phenoxy primer coating on a metallic stent exhibits another embodiment of the present invention.

After cleaning, an 18 millimeter S670 stent is dipped into a phenoxy resin solution for five seconds. The stent is withdrawn from the solution and spun at 1000 rpm. The phenoxy-coated stent is cured at 210 degrees centigrade for ten minutes. Drying at the elevated temperature is done in a vacuum oven after one or more nitrogen purges. Parameters for dip-coating the stent includes an entry speed of twenty millimeters per second, a dip time of ten seconds, and a withdrawal rate of five millimeters per second. The stent is rotated at 500 rpm during retraction from the phenoxy resin solution.

After cleaning, one-inch by three-inch metal coupons are dipped into the phenoxy resin solution for five seconds. The coupons are then pulled out and cured at 210 degrees centigrade for ten minutes. The coated coupons are not spun.

Using the above parameters, the coating on the stent weighs 60+/−20 micrograms, whereas the coating on the coupon weighs 2000+/−20 micrograms. With this amount of material, the phenoxy primer coating is approximately 0.4 microns to 0.6 microns thick.

EXAMPLE 3

Dry Crosshatch Adhesion Test

An adhesion test is run to verify the adhesion strength of the phenoxy primer coating to the coupons, in accordance with another embodiment of the present invention. The primer is coated onto stainless steel coupons. Eleven vertical and horizontal cuts, one millimeter apart, are scribed onto the coupons. One inch Permacel 99 tape is applied over the crosshatch area and smoothed with a finger. Within 90+/−30 seconds after application, the tape is pulled at an angle of 180 degrees. The cross-hatched grid is then examined with an optical microscope for any removal of the coating. No delamination is observed for phenoxy primer coated coupons.

EXAMPLE 4

Wet Crosshatch Adhesion Test

A wet adhesion test is run to verify the adhesion strength of the phenoxy primer coating to the coupons, in accordance with another embodiment of the present invention. The primer is coated onto stainless steel coupons and crosshatched as in Example 3. The coupons are immersed in a phosphate-buffered saline solution for one hour at 37 degrees centigrade. The coupons are removed and dried with a lint-free cloth, and then Permacel tape is applied to the coating and pulled after 90+/−30 seconds following application. The adhesion rating of this method is similar to the dry crosshatch method of Example 3. No delamination is observed for phenoxy primer coated coupons.

EXAMPLE 5

Simulated Lesion Abrasion Test

A durability test is run to simulate the abrasion that a coating might experience in the area of a lesion that needs dilating. To help assess the integrity of the phenoxy primer coating on a stent, a stent is passed multiple times through a silicon tube of a prescribed outer diameter and inner diameter, after which the stent is deployed. The durability test is followed by optical microscope inspection and scanning electron microscope inspection. All phenoxy-coated stents pass the simulated lesion abrasion test.

EXAMPLE 6

Cytotoxicity Study

A cytotoxicity study is conducted to test potential cytotoxicity. A cyctotoxicity test in accordance with ISO 10993-5 and USP 24 section 87 performed on the phenoxy primer coating shows no evidence of cell toxicity after twenty-four hours.

EXAMPLE 7

Hemolysis Study

A hemolysis study is conducted to test affinity for hemolysis. The hemolysis study is carried out with phenoxy-coated samples. Positive-control samples use 0.1% sodium carbonate in sterile water, and negative-control samples use polypropylene pellets. Positve and negative control samples are contacted with rabbit blood and incubated at 37 degrees centigrade for one hour. The results indicate 0% hemolysis for the phenoxy-coated samples.

Although the present invention applies to cardiovascular and endovascular stents with timed-release pharmaceutical drugs, the use of primer coatings under polymer-drug coatings may be applied to other implantable and blood-contacting biomedical devices such as coated pacemaker leads, microdelivery pumps, feeding and delivery catheters, heart valves, artificial livers and other artificial organs.

What is claimed is:

1. A system for treating a vascular condition, comprising:
   a catheter;
   a stent coupled to the catheter, the stent including a stent framework;
   a phenoxy resin coating operably disposed on the stent framework; and a drug-polymer coating disposed on the phenoxy resin coating.

2. The system of claim 1 wherein the catheter includes a balloon used to expand the stent.

3. The system of claim 1 wherein the catheter includes a sheath that retracts to allow expansion of the stent.

4. The system of claim 1 wherein the stent framework comprises a metallic base.

5. The system of claim 1 wherein the stent framework comprises a material selected from the group consisting of stainless steel, nitinol, tantalum, MP35N alloy, platinum, titanium, a suitable biocompatible alloy, a suitable biocompatible material, and a combination thereof.

6. The system of claim 1 wherein the phenoxy resin coating has a thickness between 0.2 and 0.6 microns.

7. The system of claim 1 wherein the phenoxy resin coating has a weight between 20 and 70 micrograms.

8. The system of claim 1 wherein the phenoxy resin coating includes a cross-linking agent.

9. The system of claim 8 wherein the cross-linking agent comprises isocyanate.

10. The system of claim 1 wherein the drug-polymer coating comprises a bioactive agent.

11. The system of claim 10 wherein the bioactive agent is selected from the group consisting of an antisense agent, an antineoplastic agent, an antiproliferative agent, an antithrombogenic agent, an anticoagulant, an antiplatelet agent, an antibiotic, an anti-inflammatory agent, a gene therapy agent, a therapeutic substance, an organic drug, a pharmaceutical compound, a recombinant DNA product, a recombinant RNA product, a collagen, a collagenic derivative, a protein, a protein analog, a saccharide, and a saccharide derivative.

12. The system of claim 1 wherein the phenoxy resin coating comprises a phenoxy resin comprising hydroxyl groups.

13. The system of claim 1 wherein the phenoxy resin coating comprises a long-chain polymer with predominantly phenoxyl groups along the backbone.

14. A drug-coated stent, comprising:
a stent framework;
a phenoxy resin coating disposed on the stent framework; and
a drug-polymer coating disposed on the phenoxy resin coating.

15. The drug-coated stent of claim 14 wherein the stent framework comprises a metallic base.

16. The drug-coated stent of claim 14 wherein the stent framework comprises a material selected from the group consisting of stainless steel, nitinol, tantalum, MP35N alloy, platinum, titanium, a suitable biocompatible alloy, a suitable biocompatible material, and a combination thereof.

17. The drug-coated stent of claim 14 wherein the phenoxy resin coating has a thickness between 0.2 and 0.6 microns.

18. The drug-coated stent of claim 14 wherein the phenoxy resin coating has a weight between 20 and 70 micrograms.

19. The drug-coated stent of claim 14 wherein the phenoxy resin coating includes a cross-linking agent.

20. The drug-coated stent of claim 19 wherein the cross-linking agent comprises isocyanate.

21. The drug-coated stent of claim 14 wherein the drug-polymer coating comprises a bioactive agent.

22. The drug-coated stent of claim 21 wherein the bioactive agent is selected from the group consisting of an antisense agent, an antineoplastic agent, an antiproliferative agent, an antithrombogenic agent, an anticoagulant, an antiplatelet agent, an antibiotic, an anti-inflammatory agent, a gene therapy agent, a therapeutic substance, an organic drug, a pharmaceutical compound, a recombinant DNA product, a recombinant RNA product, a collagen, a collagenic derivative, a protein, a protein analog, a saccharide, and a saccharide derivative.

23. The stent of claim 14 wherein the phenoxy resin coating comprises a phenoxy resin comprising hydroxyl groups.

24. The stent of claim 14 wherein the phenoxy resin coating comprises a long-chain polymer with predominantly phenoxyl groups along the backbone.

* * * * *